(12) United States Patent  
Welker et al.

(10) Patent No.: US 11,642,225 B2  
(45) Date of Patent: May 9, 2023

(54) POLY-FACED BONE FUSION IMPLANT

(71) Applicant: In2Bones USA, LLC, Memphis, TN (US)

(72) Inventors: David M. Welker, Memphis, TN (US); Alan G. Taylor, Memphis, TN (US); Rebecca Hawkins Wahl, Escondido, CA (US)

(73) Assignee: In2Bones USA, LLC, Memphis, TN (US)

( * ) Notice: Subject to any disclaimer, the term of this patent is extended or adjusted under 35 U.S.C. 154(b) by 128 days.

(21) Appl. No.: 16/904,426

(22) Filed: Jun. 17, 2020

(65) Prior Publication Data

US 2020/0323640 A1    Oct. 15, 2020

Related U.S. Application Data

(62) Division of application No. 15/901,774, filed on Feb. 21, 2018, now Pat. No. 10,709,567.

(60) Provisional application No. 62/462,766, filed on Feb. 23, 2017.

(51) Int. Cl.

| | |
|---|---|
| *A61F 2/42* | (2006.01) |
| *A61F 2/46* | (2006.01) |
| *A61B 17/68* | (2006.01) |
| *A61B 17/72* | (2006.01) |

(Continued)

(52) U.S. Cl.  
CPC ............. *A61F 2/4225* (2013.01); *A61B 17/68* (2013.01); *A61B 17/7283* (2013.01); *A61B 17/7291* (2013.01); *A61F 2/4606* (2013.01); *A61F 2002/2839* (2013.01); *A61F 2002/30281* (2013.01); *A61F 2002/30622* (2013.01); *A61F 2002/30828* (2013.01); *A61F 2002/30884* (2013.01); *A61F 2002/4228* (2013.01); *A61F 2002/4233* (2013.01); *A61F 2310/00359* (2013.01)

(58) Field of Classification Search  
CPC ........ A61F 2/42; A61F 2/4225; A61F 2/4241; A61F 2/4606; A61B 17/68; A61B 17/7291; A61B 17/7283  
See application file for complete search history.

(56) References Cited

U.S. PATENT DOCUMENTS

| | | |
|---|---|---|
| 5,716,358 A | 2/1998 | Ochoa |
| 10,653,462 B2 * | 5/2020 | Chen ................ A61B 17/7233 |
| 2014/0309747 A1 | 10/2014 | Taylor |

* cited by examiner

*Primary Examiner* — Brian A Dukert  
(74) *Attorney, Agent, or Firm* — Rutan & Tucker LLP; Hani Z. Sayed

(57) ABSTRACT

A bone fusion implant is provided for treating conditions of Proximal Interphalangeal (PIP), Distal interphalangeal (DIP), and metatarsophalangeal (MTP) foot joints. The bone fusion implant may be a cortical bone allograft sized to fuse the foot joint to be treated. A proximal portion of the implant may be pressed into a hole drilled in a proximal bone portion of the foot joint, and a distal portion of the implant may be pressed into a hole drilled in a distal bone portion of the foot joint. Ramps on the proximal and distal portions facilitate press-fitting the implant into the holes in the bone portions. Side ramps ensure that the bone fusion implant remains substantially aligned with the foot joint while the distal portion is pressed into the hole into the distal bone portion. Grooves on the ramps alleviate pressure and ease inserting the implant into the holes in the bone portions.

6 Claims, 6 Drawing Sheets

(51) Int. Cl.
*A61F 2/30* (2006.01)
*A61F 2/28* (2006.01)

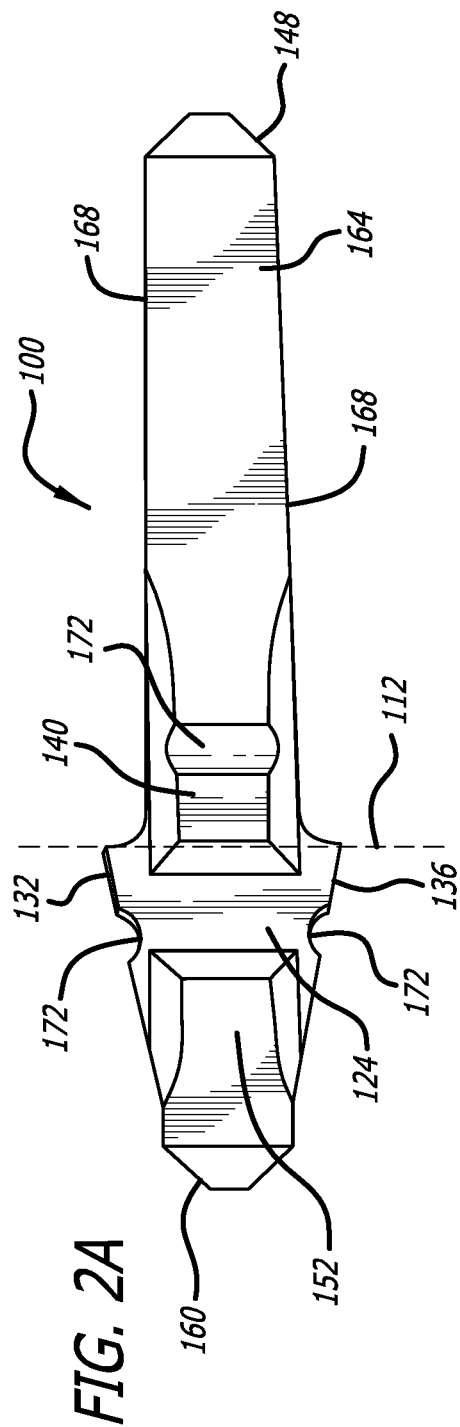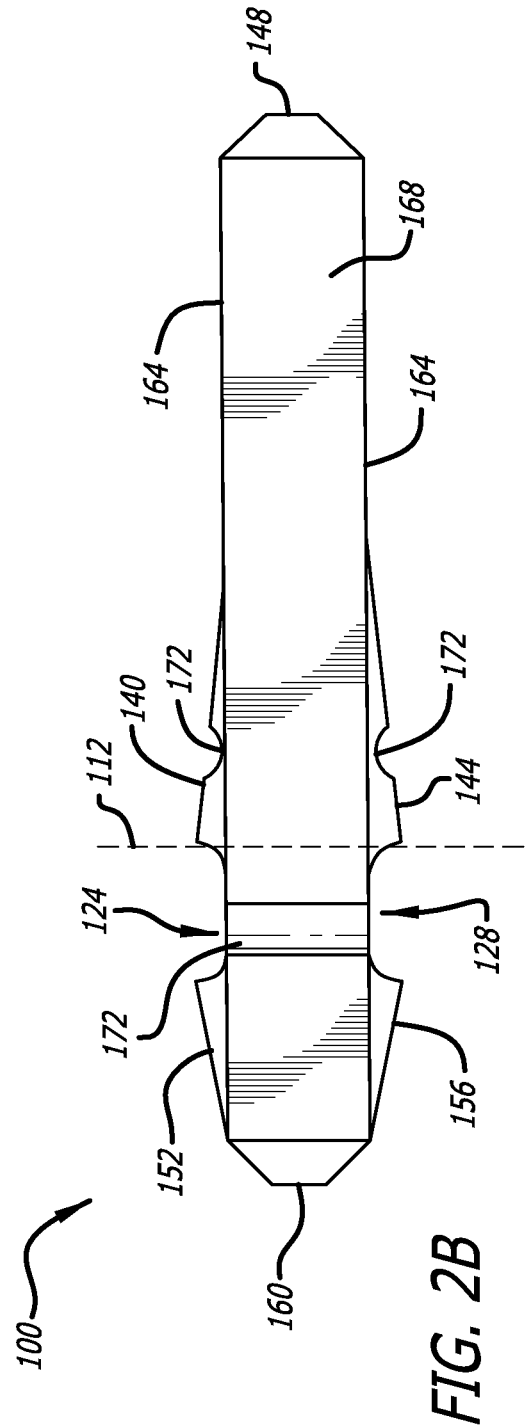
FIG. 2A
FIG. 2B

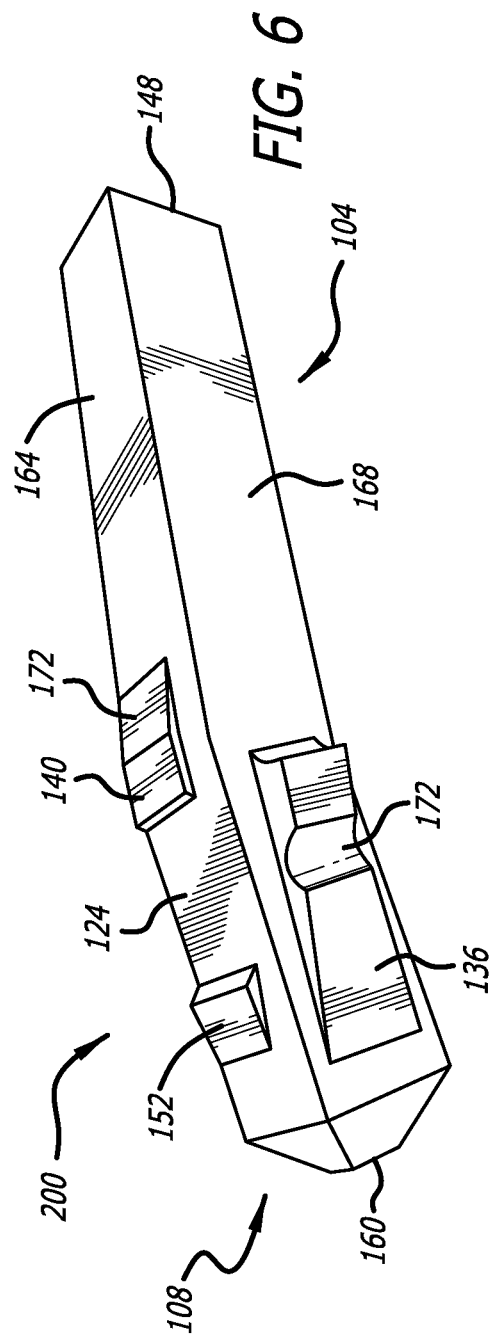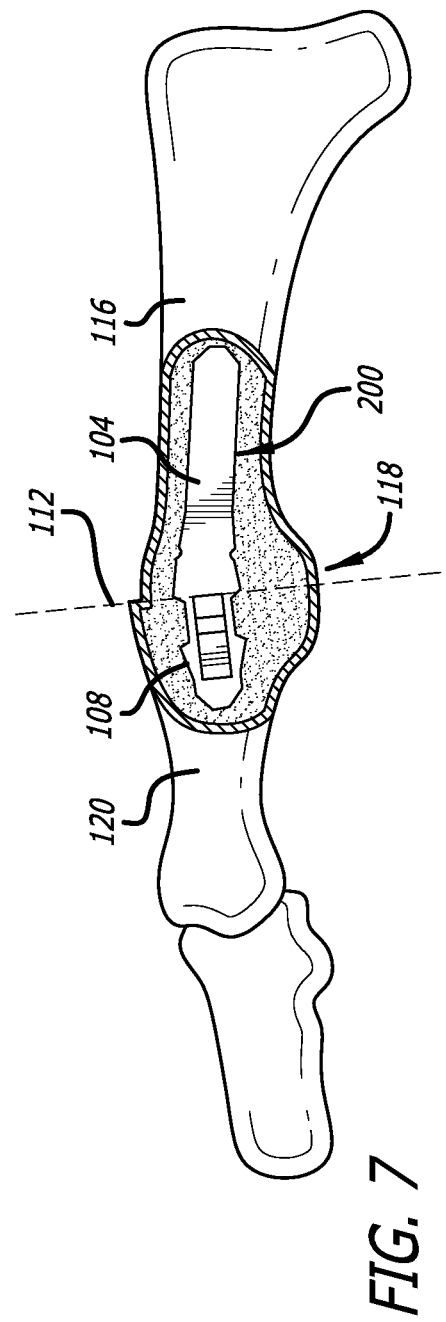

POLY-FACED BONE FUSION IMPLANT

PRIORITY

This application claims the benefit of and priority to U.S. patent application Ser. No. 15/901,774 filed on Feb. 21, 2018 and U.S. Provisional Application, entitled "Poly-Faced Bone Fusion Implant," filed on Feb. 23, 2017 and having application Ser. No. 62/462,766.

FIELD

The field of the present disclosure generally relates to securing bones together. More particularly, the field of the invention relates to an implant for fusing foot joint bones of the human body.

BACKGROUND

Proximal Interphalangeal (PIP) foot joint fusion essentially fixes the joint and fuses the proximal and middle phalanx (toe bones) in a straightened or angled position. The PIP is the first joint of the small toes. An indication for surgery is when this joint has a fixed curve deformity, such as due to claw toe, hammer toe, or mallet toe deformities. The deformity may be producing enough pain or functional limitations to warrant surgery. The deformity generally develops gradually and thus becomes fixed in a bent position for a long period of time.

There are a variety of ways that a PIP foot joint fusion may be performed. The PIP foot joint may be approached either through a longitudinal or transverse incision on the top of the toe. Once the joint is opened up, a small segment of bone may be removed from either side of the joint, creating enough room for the joint to be realigned. The joint may then be fixated in a straightened or slightly angled position, either by way of a wire or an internal screw. Fixating the PIP foot joint may be performed in association with other procedures, such as a tendon transfer, to help keep the toe in the newly straightened position, as well as procedures to address underlying mechanical problems that may have caused the small toe deformities of the PIP foot joint.

SUMMARY

A bone fusion implant is provided for fixating adjacent bone portions across a bone fusion site, particularly for treating conditions of Proximal Interphalangeal (PIP), Distal interphalangeal (DIP), and metatarsophalangeal (MTP) foot joints. The bone fusion implant is comprised of an elongate member having a proximal portion and a distal portion that share a line of fixation. A multiplicity of valleys may be disposed on opposite sides of the elongate member and configured to receive an insertion tool. A multiplicity of ramps and longitudinal grooves may be disposed on opposite sides of the elongate member. In one embodiment, proximal ramps are disposed on opposite sides of the proximal portion and extend to the line of fixation, distal ramps are disposed on opposite sides of the distal portion and extend toward the line of fixation, and side ramps are disposed between the distal ramps and extend to the line of fixation. In some embodiments, one or more longitudinal grooves may be disposed along the proximal portion and parallel the proximal ramps, and a keel may separate pairs of adjacent longitudinal grooves. The bone fusion implant may be comprised of a cortical bone allograft that is suitably sized to fuse a bone joint to be treated. A longitudinal axis of the cortical bone allograft may be substantially aligned with the longitudinal axis of the cortical bone to accommodate anisotropy in the structure of the cortical bone.

In an exemplary embodiment, a bone fusion implant for treating conditions of Proximal Interphalangeal (PIP), Distal interphalangeal (DIP), and metatarsophalangeal (MTP) foot joints comprises an elongate member comprising a proximal portion and a distal portion that share a line of fixation; proximal ramps disposed on opposite sides of the proximal portion and extending to the line of fixation; distal ramps disposed on opposite sides of the distal portion and extending toward the line of fixation; and side ramps disposed between the distal ramps and extending to the line of fixation.

In another exemplary embodiment, the bone fusion implant further comprises a dorsal valley and a plantar valley disposed between the distal ramps and the proximal ramps, the dorsal valley and the plantar valley being configured to receive an insertion tool suitable for grasping and inserting the bone fusion implant into bone. In another exemplary embodiment, the proximal portion is configured to be implanted into a hole drilled in a proximal bone portion, and wherein the distal portion is configured to be implanted into a hole drilled in a distal bone portion, the proximal bone portion and the distal bone portion comprising a bone joint being treated. In another exemplary embodiment, the side ramps are configured to contact the proximal bone portion when the line of fixation is aligned with the outside surface of the proximal bone portion, and wherein the side ramps are configured to ensure that the line of fixation remains substantially aligned with the outside surface during pressing of the distal portion into a hole drilled into the distal bone portion.

In another exemplary embodiment, the bone fusion implant is comprised of a cortical bone allograft that is suitably sized to fuse a bone joint to be treated, a longitudinal axis of the cortical bone allograft being substantially aligned with the longitudinal axis of the cortical bone to accommodate anisotropy in the structure of the cortical bone. In another exemplary embodiment, the proximal ramps are configured to facilitate press-fitting the proximal portion into a hole drilled in a proximal bone portion and create relatively greater compression between the proximal portion and the bone near the line of fixation. In another exemplary embodiment, the distal ramps are configured to facilitate press-fitting the distal portion into a bone hole drilled in a distal bone portion and encourage bone graft incorporation.

In another exemplary embodiment, the elongate member has at least four sides, such that two opposite of the at least four sides include the proximal ramps and comprise substantially parallel faces of the elongate member between the proximal ramps and a proximal end of the elongate member, and such that two opposite of the at least four sides include the distal ramps and comprise tapered faces of the elongate member between the side ramps and the proximal end, the tapered faces being configured to facilitate a press-fit between the proximal portion and a hole drilled in bone. In another exemplary embodiment, one or more transverse grooves are disposed on any one or more of the side ramps, the proximal ramps, and the distal ramps, the transverse grooves being configured to alleviate pressure and ease inserting the bone fusion implant into a hole drilled in bone. In another exemplary embodiment, any one or more of the side ramps, the proximal ramps, and the distal ramps include a surface texture configured to ease inserting the bone fusion implant into a hole drilled in bone and facilitate bone graft incorporation. In another exemplary embodiment, the surface texture is biased toward the line of fixation so as to facilitate movement of bone toward the line of fixation and inhibit bone movement away from the line of fixation.

In another exemplary embodiment, one or more longitudinal grooves are disposed on any one or more of the side ramps, the proximal ramps, and the distal ramps, the longitudinal grooves being configured to ease inserting the bone fusion implant into a hole drilled in bone and facilitate bone graft incorporation. In another exemplary embodiment, one or more longitudinal grooves are disposed along the proximal portion and configured to facilitate inserting the bone fusion implant into bone and encourage bone graft incorporation. In another exemplary embodiment, the proximal portion is disposed at a longitudinal angle with respect to the distal portion, the longitudinal angle being configured such that a bone joint may be fixated with a distal bone portion oriented in a plantar direction relative to a proximal bone portion. In another exemplary embodiment, at least a portion of the elongate member comprises a curved portion that directs the distal portion at the longitudinal angle relative to the proximal portion.

In an exemplary embodiment, a bone fusion implant for fixating adjacent bone portions across a bone fusion site comprises an elongate member comprised of a proximal portion and a distal portion that share a line of fixation; a multiplicity of valleys disposed on opposite sides of the bone fusion implant and configured to receive an insertion tool; a multiplicity of ramps comprising longitudinal grooves and disposed on opposite sides of the bone fusion implant; one or more longitudinal grooves disposed along the proximal portion and paralleling the proximal ramps; and a keel separating each pair of adjacent of the one or more longitudinal grooves.

In another exemplary embodiment, the proximal portion is configured to be implanted into a portion of a bone hole drilled in a proximal bone portion and the distal portion is configured to be implanted into a portion of the bone hole drilled in a distal bone portion across the bone fusion site. In another exemplary embodiment, the multiplicity of valleys is comprised of distal valleys disposed near the line of fixation and proximal valleys disposed near a proximal end of the bone fusion implant. In another exemplary embodiment, the multiplicity of ramps is comprised of distal ramps disposed on the distal portion and configured to contact a distal bone portion, and wherein the multiplicity of ramps is comprised of proximal ramps disposed on the proximal portion and configured to contact a proximal bone portion. In another exemplary embodiment, the one or more longitudinal grooves extend along the entire length of the proximal portion. In another exemplary embodiment, the one or more longitudinal grooves are comprised of at least four longitudinal grooves, and wherein at least two keels are disposed along the length of the proximal portion.

BRIEF DESCRIPTION OF THE DRAWINGS

The drawings refer to embodiments of the present disclosure in which:

FIG. 2A illustrates a top plan view of the exemplary embodiment of the bone fusion implant of FIG. 1;

FIG. 2B illustrates a side plan view of the exemplary embodiment of the bone fusion implant of FIG. 1;

FIG. 6 illustrates an isometric view of an exemplary embodiment of a bone fusion implant comprising a longitudinal bend;

FIG. 7 illustrates a cut-away view of a proximal interphalangeal foot joint being fixated at an angle by way of the bone fusion implant of FIG. 6;

Figure 1:
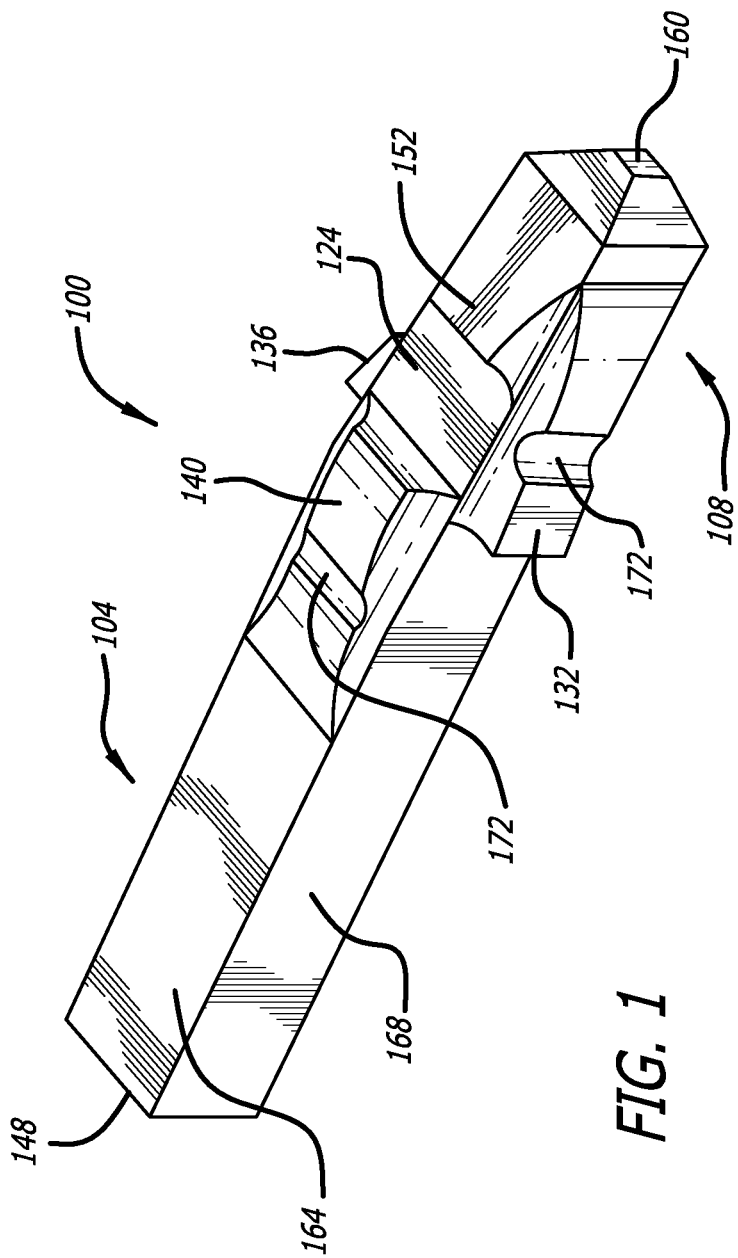
FIG. 1 illustrates an isometric view of an exemplary embodiment of a bone fusion implant that is configured to treat conditions of Proximal Interphalangeal (PIP) and Distal interphalangeal (DIP) foot joints, such as claw toe, hammer toe, and mallet toe deformities.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first bone portion," may be made. However, the specific numeric reference should not be interpreted as a literal sequential order but rather interpreted that the "first bone portion" is different than a "second bone portion." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes a bone fusion implant for treating conditions of Proximal Interphalangeal (PIP), Distal interphalangeal (DIP), and metatarsophalangeal (MTP) foot joints. The bone fusion implant comprises an elongate member having a proximal portion and a distal portion that share a line of fixation. The proximal portion is configured to be implanted into a hole drilled in a proximal bone portion of the PIP foot joint, and the distal portion is configured to be implanted into a hole drilled in a distal bone portion of the PIP foot joint. Proximal ramps are disposed on opposite sides of the proximal portion and configured to facilitate press-fitting the proximal portion into the hole in the proximal bone portion. Distal ramps are disposed on opposite sides of the distal portion and configured to facilitate press-fitting the distal portion into the hole drilled in a distal bone portion. The proximal and distal ramps create a relatively greater compression between the bone fusion implant and the portion of bone near the line of fixation. Side ramps disposed between the distal ramps and extending toward the line of fixation are configured to contact the proximal bone portion when the line of fixation is aligned with the outside surface of the proximal bone portion. The side ramps ensure that the line of fixation remains substantially aligned with the PIP foot joint during pressing of the distal portion into the hole drilled into the distal bone portion. A dorsal valley and a plantar valley are disposed between the distal ramps and the proximal ramps. The dorsal and plantar valleys are configured to receive an insertion tool suitable for grasping and inserting the bone fusion implant into the hole drilled in proximal bone portion.

FIG. 1 illustrates an exemplary embodiment of a bone fusion implant 100 that is configured to treat conditions of PIP, DIP, and MTP foot joints. Such conditions may include, but are not limited to claw toe, hammer toe, and mallet toe deformities. The bone fusion implant 100 may be comprised of a cortical bone allograft that is suitably sized to fuse the PIP, DIP, and MTP joints of the foot. It is contemplated that a longitudinal axis of the cortical bone allograft may be substantially aligned with the longitudinal axis of the cortical bone to accommodate anisotropy in the structure of the cortical bone.

Figure 3:
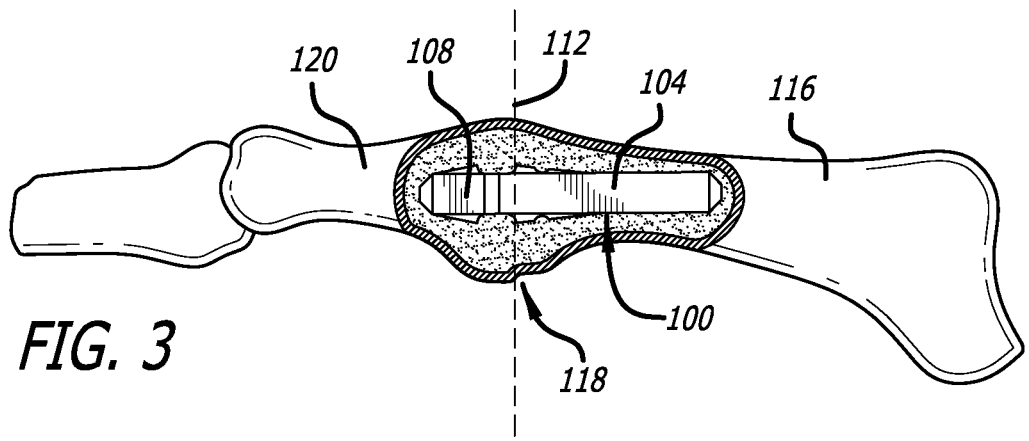
FIG. 3 illustrates a cut-away view of a proximal interphalangeal foot joint being fixated by way of the bone fusion implant of FIG. 1.
Figure 4:
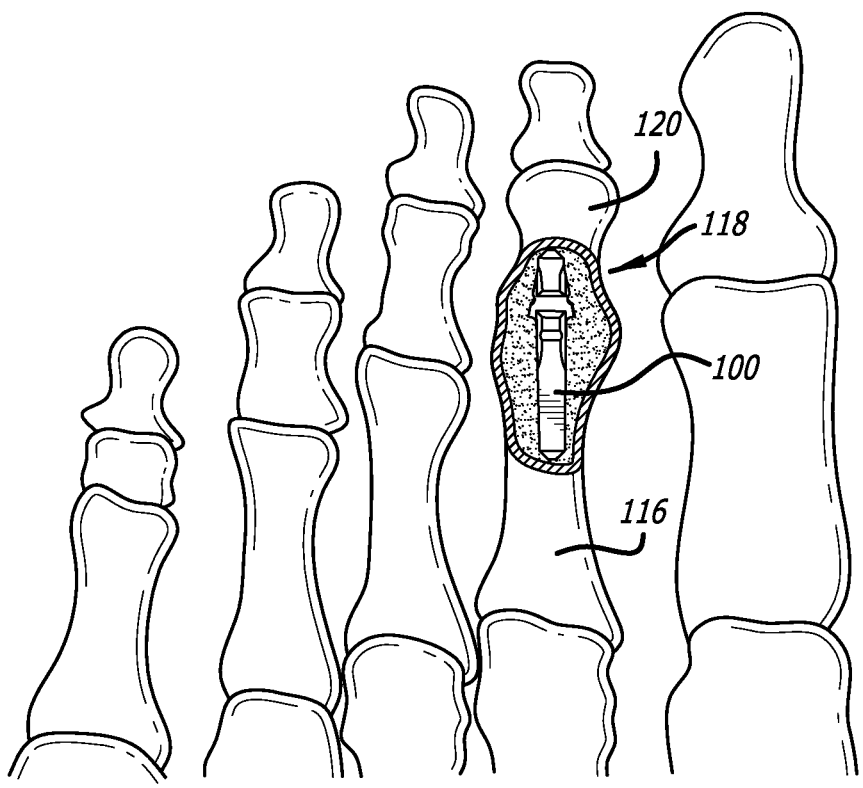
FIG. 4 illustrates a cut-away dorsal-plantar view of a proximal interphalangeal foot joint being fixated by way of the bone fusion implant of FIG. 1.

The bone fusion implant 100 is a generally elongate member comprised of a proximal portion 104 and a distal portion 108 that share a line of fixation 112 shown in FIGS. 2A-2B. The proximal portion 104 is configured to be implanted into a hole drilled in a proximal bone portion 116, such as a proximal phalanx of a PIP foot joint 118, as shown in FIGS. 3 and 4. The distal portion 108 is configured to be implanted into a hole drilled in a distal bone portion 120, such as a middle phalanx of the PIP foot joint 118. In the illustrated embodiment, the length of the proximal portion 104 is relatively greater than the length of the distal portion 108. The lengths of the proximal and distal portions 104, 108 are configured to optimize insertion of the bone fusion implant 100 into PIP, DIP, and MTP foot joints, as described herein. In general, however, the lengths of the proximal and distal portions 104, 108 are dependent upon the characteristics of the specific bone portions to be fused, or fixated, and thus the lengths of the proximal and distal portions 104, 108 may be varied from those shown herein, without limitation.

During fusing the PIP foot joint 118, the proximal portion 104 may be inserted into the proximal bone portion 116 by way of an insertion tool suitable for grasping and pushing the bone fusion implant 100 into bone, such as, by way of non-limiting example, forceps or other similar tool. A dorsal valley 124 and a plantar valley 128 disposed on opposite faces of the distal portion 108 are configured to receive the insertion tool. Upon grasping the bone fusion implant 100 by way of the dorsal and plantar valleys 124, 128, the proximal portion 104 may be pressed into the hole in the proximal bone portion 116. Side ramps 132, 136, disposed adjacent to the valleys 124, 128 on opposite faces of the bone fusion implant 100, are configured to contact the proximal bone portion 116 when the line of fixation 112 is aligned with the outside surface of the proximal bone portion 116. The distal bone portion 120 may be pressed onto the distal portion 108 that remains extending outside the proximal bone portion 116. The side ramps 132, 136 ensure that the line of fixation 112 remains substantially aligned with the PIP foot joint 118 during pressing the distal portion 108 into the hole drilled into the distal bone portion 120.

As best illustrated in FIG. 2B, proximal ramps 140, 144 are disposed on opposite sides of the proximal portion 104. The proximal ramps 140, 144 comprise a tapered thickness of the proximal portion 104 extending away from the valleys 124, 128 toward a proximal end 148. As will be recognized, the proximal ramps 140, 144 facilitate press-fitting the proximal portion 104 into the hole drilled in the proximal bone portion 116 and create relatively greater compression between the proximal portion 104 and the bone near the line of fixation 112. Further, the proximal ramps 140, 144 discourage loosening of the proximal portion 104 within the proximal bone portion 116 after being press-fitted into the bone hole.

As further shown in FIG. 2B, distal ramps 152, 156 are disposed on opposite sides of the distal portion 108. The distal ramps 152, 156 are similar to the proximal ramps 140, 144, with the exception that the distal ramps 152, 156 comprise a tapered thickness of the distal portion 108 extending away from the valleys 124, 128 toward a distal end 160. The distal ramps 152, 156 facilitate press-fitting the distal portion 108 into a bone hole drilled in the distal bone portion 120. Similar to the ramps 140, 144, the distal ramps 152, 156 are configured to create a relatively greater compression between the distal portion 108 and the bone near the line of fixation 112. As shown in FIG. 2B, the distal ramps 152, 156 slope toward the distal end 160, thereby facilitating inserting the distal portion 108 into the bone hole and discouraging loosening of the compression between the distal portion 108 and the distal bone portion 120.

As shown in FIGS. 2A-2B, the proximal and distal ends 148, 160 may be chamfered so as to the minimize resistance to inserting the bone fusion implant 100 into bone. It should be understood, however, that the proximal and distal ends 148, 160 need not be chamfered as shown in FIGS. 2A-2B, but rather the proximal and distal ends 148, 160 may include any of various surface features that are found to facilitate inserting the proximal and distal ends 148, 160 into holes drilled in bone. For example, the proximal and distal ends 148, 160 may be beveled at any of various angles, as desired, or rounded to minimize potential trauma to bone surrounding the hole drilled in bone.

In the embodiment of the bone fusion implant 100 illustrated in FIGS. 2A-2B, the generally elongate member comprising the bone fusion implant has four-sides. As shown in FIG. 2B, two opposite sides, upon which the proximal and distal ramps 140-156 are disposed, comprise substantially parallel faces 164 of the bone fusion implant 100 between the proximal ramps 140, 144 and the proximal end 148. The two opposite sides that include the side ramps 132, 136 comprise angled, or tapered faces 168 of the bone fusion implant 100 between the side ramps and the proximal end 148. The tapered faces 168 are configured to facilitate a press-fit between the proximal portion 104 and the bone hole drilled into the proximal bone portion 116. It is contemplated that the press-fit may discourage loosening of the bone fusion implant 100 within the bone and encourage graft incorporation.

The bone fusion implant 100 need not be limited to four-sides, but rather the elongate member comprising a poly-faced bone fusion implant may be comprised of greater than four sides. For example, in some embodiments, the elongate member comprising the poly-faced bone fusion implant may have five, six, seven, eight, or any number of sides that is found to facilitate fusing the PIP, DIP, and MTP foot joints, as described herein. Further, the poly-faced bone fusion implant is not limited to being comprised of the side, proximal, and distal ramps 132-156 described and shown herein. In some embodiments, for example, the poly-faced bone fusion implant may be comprised of more than two distal ramps 152, 156, such as four distal ramps without limitation. In some embodiments, the poly-faced bone fusion implant may be comprised of more than two proximal ramps 140, 144, such as, by way of non-limiting example, four proximal ramps.

Moreover, the poly-faced bone fusion implant may be comprised of various numbers of side, proximal, and distal ramps without limitation. For example, in one embodiment, the elongate member comprising the poly-faced bone fusion implant may be comprised of eight sides with four distal ramps and four side ramps uniformly distributed around the perimeter of the distal portion 108. Further, such an embodiment of the poly-faced bone fusion implant may be comprised of four or eight proximal ramps that are uniformly distributed around the perimeter of the proximal portion 104, without limitation.

In some embodiments, transverse grooves 172 may be disposed on any of the side, proximal, and distal ramps 132-156. In the embodiment illustrated in FIGS. 2A and 2B, transverse grooves 172 are disposed in the side ramps 132, 136 and the proximal ramps 140, 144. The transverse grooves 172 may alleviate pressure and ease inserting the bone fusion implant 100 into the bone. The transverse grooves 172 may further increase the surface area of the bone fusion implant 100 so as to encourage graft incorporation. Once the bone fusion implant 100 has been suitably inserted into the bone, the bone may grow into the transverse grooves 172 and thereby maintain fixation of the implant in the bone. Moreover, it is contemplated that in some embodiments, any of various surface textures or other topological features may be incorporated into any one or more of the ramps 132-156, either in addition to or in lieu of the transverse grooves 172. For example, in some embodiments, the ramps 132-156 may each be comprised of a multiplicity of smaller transverse grooves disposed adjacently along the surface of each ramp. In some embodiments, the smaller transverse grooves may be biased toward the dorsal and plantar valleys 124, 128 so as to form sawtooth textures that facilitate movement of bone toward the line of fixation 112 and inhibit bone movement away from the line of fixation.

Figure 5A:
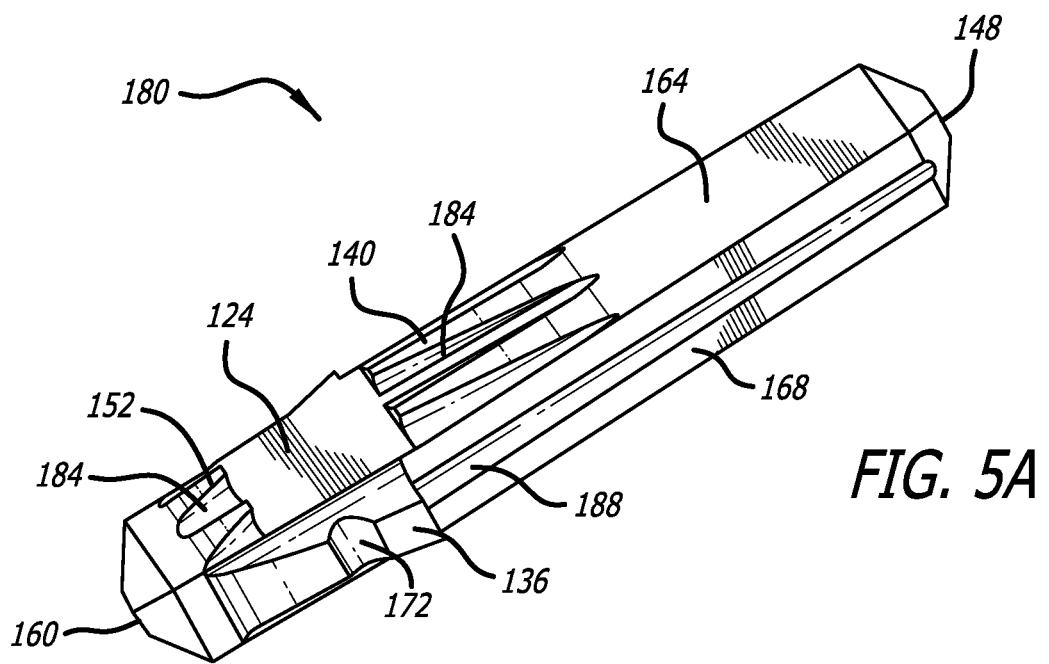
FIG. 5A illustrates an isometric view of an exemplary embodiment of a bone fusion implant comprising longitudinal and transverse grooves.
Figure 5B:
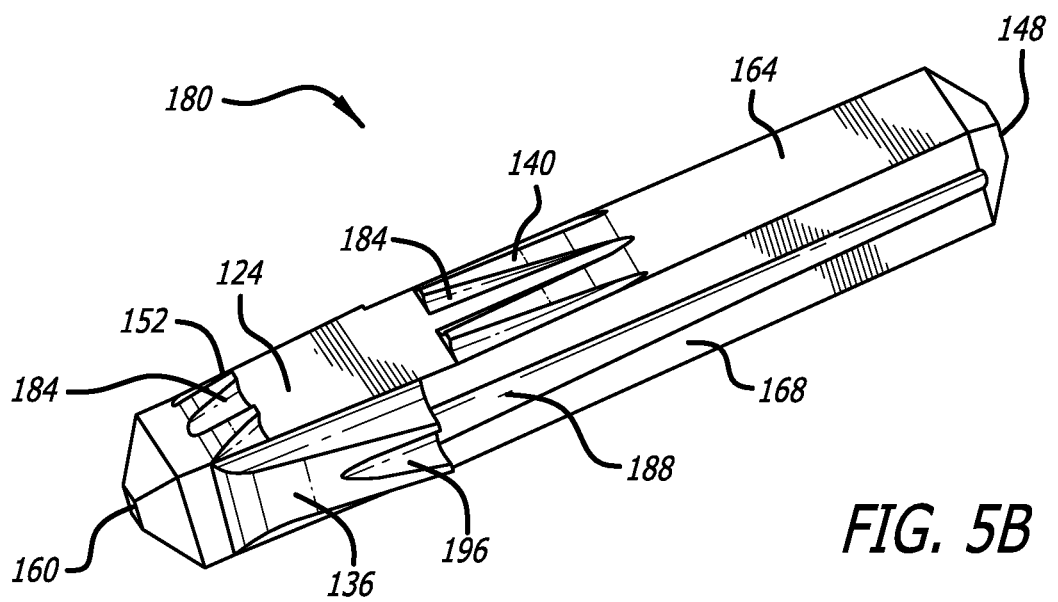
FIG. 5B illustrates an isometric view of an exemplary embodiment of a bone fusion implant comprising multiple longitudinal grooves.

FIG. 5A illustrates an isometric view of an exemplary embodiment of a bone fusion implant 180 that is configured to treat deformities of PIP and DIP foot joints. The bone fusion implant 180 is substantially similar to the bone fusion implant 100, illustrated in FIG. 1, with the exception that the bone fusion implant 180 is comprised of proximal and distal ramps 140-156 that include longitudinal grooves 184, in lieu of the transverse grooves 172. Further, the bone fusion implant 180 comprises a longitudinal groove 188 disposed in each of the tapered faces 168. FIG. 5B illustrates an exemplary embodiment of a bone fusion implant 192 that comprises a longitudinal groove 196 disposed in each of the side ramps 132, 136 in lieu of the transverse grooves 172. The longitudinal grooves 184, 188, 196 are configured to facilitate inserting the bone fusion implant into bone and encourage bone graft incorporation, as disclosed herein.

FIG. 6 illustrates an isometric view of an exemplary embodiment of a bone fusion implant 200 that is configured to treat deformities of PIP, DIP, and MTP foot joints. The bone fusion implant 200 is substantially similar to the bone fusion implant 100, illustrated in FIG. 1, with the exception that the bone fusion implant 200 is comprised of a proximal portion 104 that is disposed at a longitudinal angle with respect to a distal portion 108. The bone fusion implant 200 may be used to fixate the PIP foot joint 118 with the distal bone portion 120 (e.g., the middle phalanx) disposed in the plantar direction, at a desired angle, relative to the proximal bone portion 116 (e.g., the proximal phalanx), as shown in FIG. 7. In some embodiments, the proximal and distal portions 104, 108 may be comprised of straight portions that are disposed at an angle with respect to one another. In some embodiments, a curved portion may be incorporated into the bone fusion implant 200 to direct the distal portion 108 at an angle relative to the proximal portion 104. In some embodiments, the bone fusion implant 200 may be comprised of a curved elongate member, wherein the distal portion 108 is disposed at angle relative to the proximal portion 104. It should be recognized, therefore, that any of various techniques may be used to establish an angle between the proximal and distal portions 104, 108, without limitation, and without deviating beyond the spirit and scope of the present disclosure.

Figure 8:
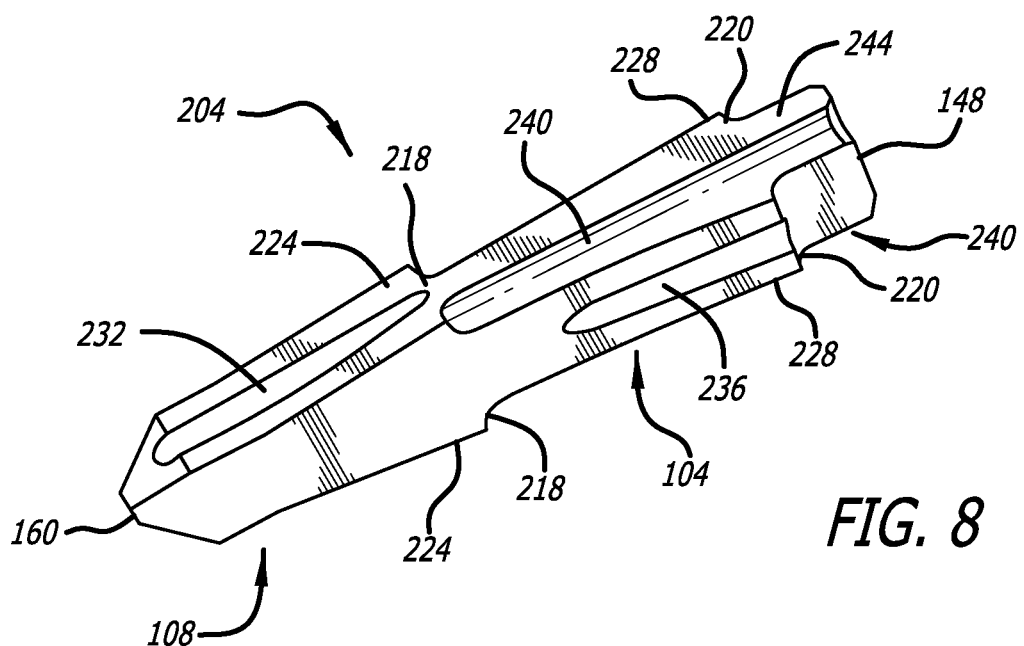
FIG. 8 illustrates an isometric view of an exemplary embodiment of a bone fusion implant comprising multiple longitudinal grooves.
Figure 9:
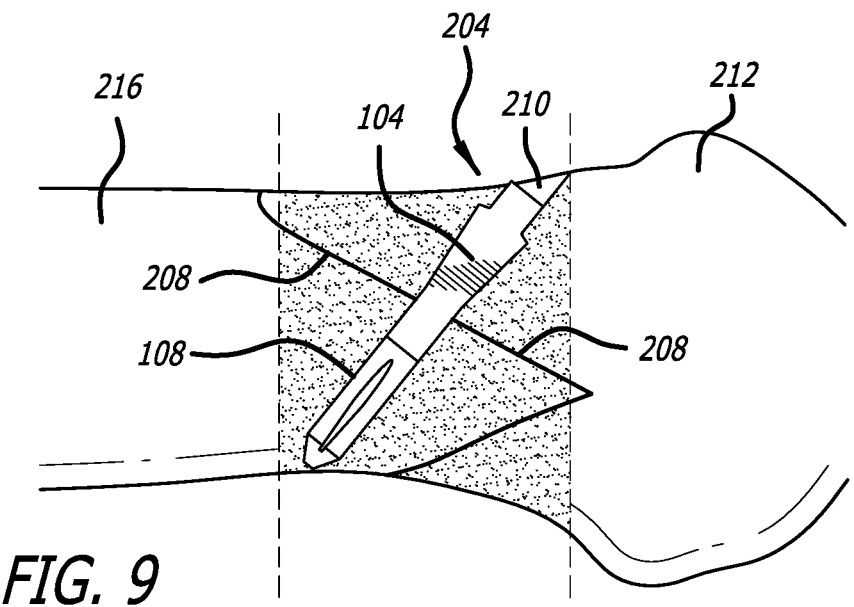
FIG. 9 illustrates a cut-away view of an exemplary osteotomy of a first metatarsal being fixated by way of the bone fusion implant of FIG. 8.

FIG. 8 illustrates an isometric view of an exemplary embodiment of a bone fusion implant 204 that may be used to treat deformities of PIP, DIP, and MTP foot joints, as well as treating other bones of the human body. The bone fusion implant 204 is a generally elongate member comprised of a proximal portion 104 and a distal portion 108 that share a line of fixation 112 that is similar to that shown in FIGS. 2A-2B. As shown in FIG. 9, the bone fusion implant 204 is configured to be implanted across a fusion site 208, wherein the proximal portion 104 is implanted into a portion of a bone hole 210 drilled in a proximal bone portion 212 and the distal portion 108 is implanted into a portion of the bone hole 210 drilled in a distal bone portion 216. As described herein, the lengths of the proximal and distal portions 104, 108 are dependent upon the characteristics of the specific bone portions to be fused, or fixated, and thus the lengths of the proximal and distal portions 104, 108 may be varied from those shown herein, without limitation.

During fusing of the proximal and distal bone portions 212, 216, the bone fusion implant 204 may be inserted into the bone hole 210 by way of an insertion tool suitable for grasping and pushing the bone fusion implant 204 into bone, such as, by way of non-limiting example, forceps or other similar tool. A pair of distal valleys 218 disposed near the line of fixation 112 are configured to receive the insertion tool. Similarly, a pair of proximal valleys 220 near the proximal end 148 may be configured to receive the insertion tool. It is contemplated that the insertion tool may be used to grasp and push the bone fusion implant 204, by way of the distal valleys 218, into the bone hole 210 until the distal valleys 218 are near the surface of the bone, at which point the proximal valleys 220 may be utilized to continue pushing the bone fusion implant deeper into the bone hole 210. The bone fusion implant 204 may be inserted into the bone hole 210 until the distal portion 108 is suitably inserted into the distal bone portion 116 and the proximal portion 104 is suitably inserted into the proximal bone portion 212, such that the line of fixation 112 is advantageously aligned with the fusion site 208.

As shown in FIG. 9, distal ramps 224 disposed on opposite sides of the distal portion 108 are configured to contact the distal bone portion 216, and proximal ramps 228 disposed on opposite sides of the proximal portion 104 are configured to contact the proximal bone portion 212. In the illustrated embodiment, the distal ramps 224 and the proximal ramps 228 flare toward the proximal end 148. In some embodiments, however, the proximal ramps 228 may flare toward the distal end 160, as discussed herein. Further, in the embodiment of the bone fusion implant 204 illustrated in FIG. 8-9, the distal ramps 224 are disposed on surfaces that are adjacent to the surfaces comprising the proximal ramps 228. In some embodiments, however, any of the distal ramps 224 and any of the proximal ramps 228 may share the same surface of the bone fusion implant 204, without limitation. Moreover, each of the distal ramps 224 includes a longitudinal groove 232, and each of the proximal ramps 228 includes a longitudinal groove 236. The longitudinal grooves 232, 236 are configured to facilitate inserting the bone fusion implant 204 into bone and encourage bone graft incorporation, as disclosed herein.

With continuing reference to FIG. 8, each of the proximal ramps 228 is adjacently paralleled by a longitudinal groove 240. The longitudinal grooves 240 generally are disposed along the entire length of the proximal portion 104, although various lengths of the longitudinal grooves are contemplated. In the illustrated embodiment of FIG. 8, the proximal portion 104 is comprised of four longitudinal grooves 240. It is envisioned, however, that more or less than four longitudinal grooves 240 may be disposed along the proximal portion 104, depending on the number of proximal ramps 228 incorporated into the proximal portion 104, without limitation. A keel 244 separates each pair of adjacent longitudinal grooves 240 and extends along the length of the proximal portion 104. Although the illustrated embodiment of FIG. 8 is comprised of two keels 244, it should be understood that more or less than two keels 244 may be incorporated into the bone fusion implant 204, depending on the number of proximal ramps 228 comprising the proximal portion 104, without limitation. Further, as mentioned with respect to the longitudinal grooves 240, various lengths of the keels 244 are contemplated within the scope of the present disclosure. It is contemplated that the longitudinal grooves 240 and the keels 244 may facilitate inserting the bone fusion implant 204 into bone and encourage bone graft incorporation, as disclosed herein.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A bone fusion implant for fixating adjacent bone portions across a bone fusion site, comprising:
   an elongate member comprised of a proximal portion and a distal portion that share a line of fixation;
   a multiplicity of valleys disposed on opposite sides of the bone fusion implant and configured to receive an insertion tool;
   a multiplicity of ramps comprising:
   longitudinal grooves disposed on opposite sides of the bone fusion implant;
   a plurality of distal ramps disposed on the distal portion and configured to contact a distal bone portion, wherein the distal ramps comprise a tapered thickness of the distal portion extending away from the multiplicity of valleys toward a distal end;
   a plurality of transverse grooves disposed on at least one of the multiplicity of ramps, wherein the transverse grooves are configured to alleviate pressure and ease insertion of the bone fusion implant into the bone;
   one or more longitudinal grooves disposed along the proximal portion and paralleling the proximal ramps; and
   a keel separating each pair of adjacent of the one or more longitudinal grooves.

2. The implant of claim 1, wherein the proximal portion is configured to be implanted into a portion of a bone hole drilled in a proximal bone portion and the distal portion is configured to be implanted into a portion of the bone hole drilled in a distal bone portion across the bone fusion site.

3. The implant of claim 1, wherein the multiplicity of valleys is comprised of distal valleys disposed near the line of fixation and proximal valleys disposed near a proximal end of the bone fusion implant.

4. The implant of claim 1, wherein the multiplicity of ramps is comprised of proximal ramps disposed on the proximal portion and configured to contact a proximal bone portion.

5. The implant of claim 1, wherein the one or more longitudinal grooves extend along the entire length of the proximal portion.

6. The implant of claim 1, wherein the one or more longitudinal grooves are comprised of at least four longitudinal grooves, and wherein at least two keels are disposed along the length of the proximal portion.

* * * * *